United States Patent [19]

Trombley, III et al.

[11] Patent Number: 5,501,674
[45] Date of Patent: Mar. 26, 1996

[54] INTRAVENOUS CATHETER WITH NEEDLE COVER AND BLOOD COLLECTION TUBE

[75] Inventors: Frederick W. Trombley, III, New Kensington; Mark Trocki, Cheswick, both of Pa.

[73] Assignee: Medrad, Inc., Pittsburgh, Pa.

[21] Appl. No.: 206,696

[22] Filed: Mar. 7, 1994

[51] Int. Cl.⁶ .................... A61M 39/24; A61M 39/00
[52] U.S. Cl. .................................... 604/247; 604/254
[58] Field of Search .................. 604/45, 246, 256, 604/167, 284, 177, 247

[56] References Cited

U.S. PATENT DOCUMENTS

| | | | |
|---|---|---|---|
| 4,177,809 | 12/1979 | Moorehead . | |
| 4,233,982 | 11/1980 | Bauer et al. | 604/256 |
| 4,261,357 | 4/1981 | Kontos | 604/167 |
| 4,311,137 | 1/1982 | Gerard | 604/284 |
| 4,369,781 | 1/1983 | Gilson et al. . | |
| 4,573,965 | 3/1986 | Russo | 604/45 |
| 4,723,955 | 2/1988 | Vaillancourt | 604/45 |
| 4,743,243 | 5/1988 | Vaillancourt | 604/45 |
| 4,857,062 | 9/1989 | Russell | 604/256 |
| 4,857,068 | 8/1989 | Kahn | 604/256 |
| 4,917,671 | 4/1990 | Chang | 604/256 |
| 4,935,012 | 6/1990 | Magre et al. . | |
| 4,952,207 | 8/1990 | Lemieux . | |
| 4,969,876 | 11/1990 | Patterson . | |
| 4,978,344 | 12/1990 | Dombrowski et al. . | |
| 5,084,023 | 1/1992 | Lemieux . | |
| 5,093,394 | 3/1992 | Luther | 604/167 |
| 5,125,903 | 6/1992 | McLaughlin et al. | 604/256 |
| 5,151,087 | 9/1992 | Jonhman | 604/256 |
| 5,163,913 | 11/1992 | Rantanen-Lee et al. | 604/177 |
| 5,195,974 | 3/1993 | Hardy | 604/110 |
| 5,201,713 | 4/1993 | Rossetti . | |
| 5,215,528 | 6/1993 | Purdy et al. . | |
| 5,300,034 | 4/1994 | Behnke et al. | 604/256 |
| 5,300,046 | 4/1994 | Scarfone et al. | 604/256 |
| 5,342,326 | 8/1994 | Peppel et al. | 604/284 |
| 5,383,860 | 1/1995 | Lau | 604/256 |

OTHER PUBLICATIONS

Advertisement Copy of IV Catheter, "Intima" from Deseret Medical—Becton Dickinson & Company, 1990.

*Primary Examiner*—Paul J. Hirsch
*Attorney, Agent, or Firm*—Keck, Mahin & Cate

[57] ABSTRACT

A catheter introducing assembly is provided which includes a self-shielding needle while providing captured visual blood flowback. The catheter introducing assembly includes a clear Y-Connector which is used for contrast injection and has an additional port for medication. A V-Spring is placed unrestricted in a spring holder which is attached to the distal end of the Y-Connector. The spring acts as a guard, once the needle is withdrawn, to protect the needle from forward movement. An injection port is provided for high pressure introduction of medication or contrast media. A silicon ball is retained in the injection port which, when medication is required, will reseal after the needle is withdrawn. A luer/filter assembly is provided in fluid communication with the introducer needle to allow air to escape through the filter for visualization of blood flowback upon needle insertion.

13 Claims, 4 Drawing Sheets

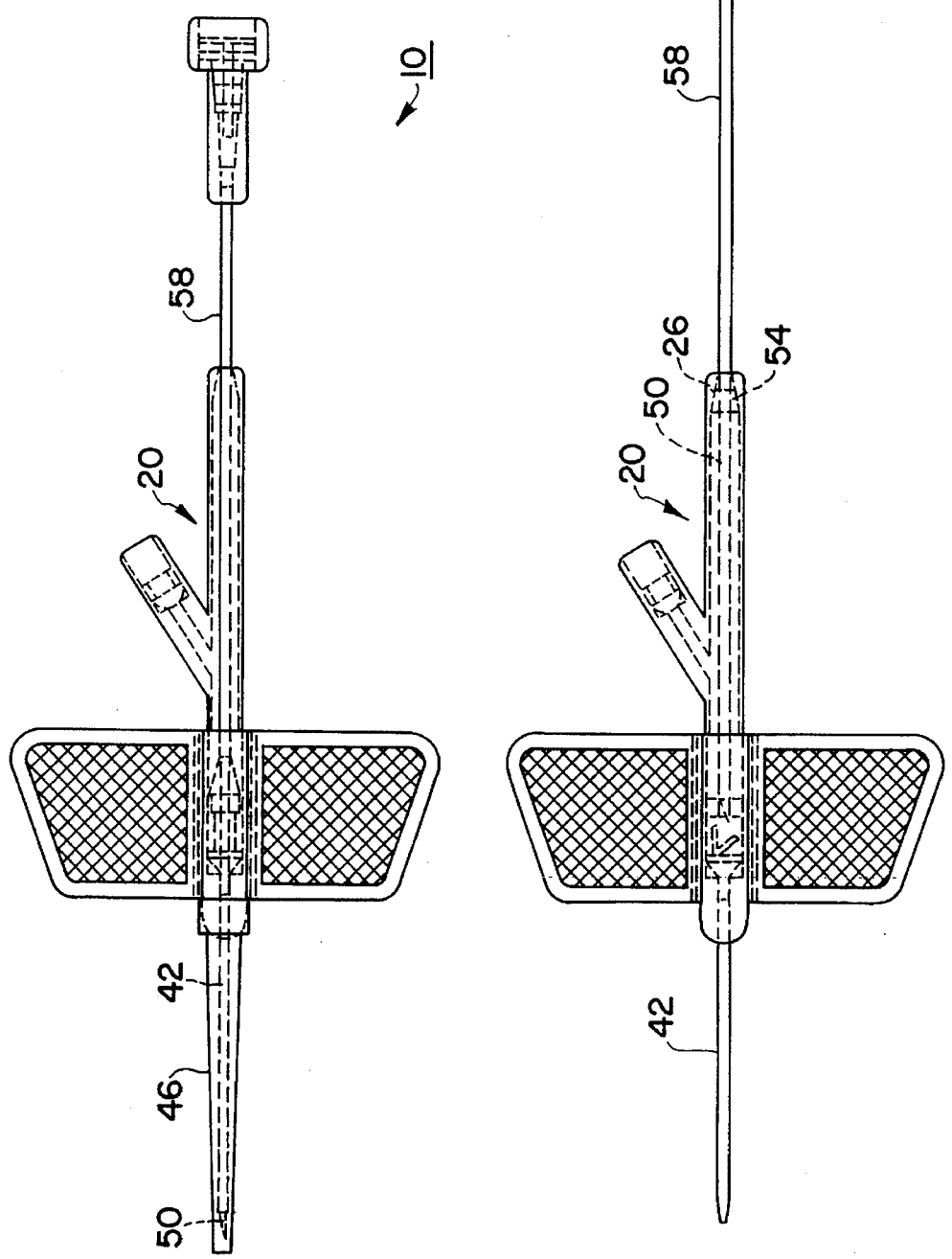

INTRAVENOUS CATHETER WITH NEEDLE COVER AND BLOOD COLLECTION TUBE

BACKGROUND OF THE INVENTION

1. Field of the Invention

This invention relates generally to intravenous ("IV") catheters, and more particularly, relates to intravenous catheters which may be used to safely convey contrast media into the venous circulatory system of a patient.

In medical procedures requiring the introduction of a catheter into blood vessels, the catheter is usually positioned over a hollow needle. Typically, the introducer needle and catheter are inserted through the skin and into the blood vessel and then the introducer needle is withdrawn through the catheter, leaving the catheter in place in the blood vessel.

It is desirable to determine by reverse flow of blood through the needle that the needle and catheter have properly pierced the blood vessel. This confirms proper catheter placement. It is also desirable to protect the health practitioner from the danger presented by an exposed needle tip contaminated with bodily fluids.

2. Description of the Prior Art

The IV Catheters most commonly used for fluid delivery are designed primarily for IV drip or low pressure injections. They are not recommended for use with CT/MRI (Computed Tomography/Magnetic Resonance Imaging) procedures or power injectors which may have high pressure in the range of 350 psi. levels.

A typical over-the-needle IV catheter requires the user to remove and then dispose of a contaminated needle after the needle tip and catheter are properly located in the vein of the patient. Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon. As the tip is quite sharp and is typically contaminated with bodily fluid, the needle may present a health risk unless steps are taken to cover the tip. For this reason, there is an increasing need to protect the user from accidental needle injury and exposure to hepatitis and AIDS.

Examples of prior art patents incorporating the use of a needle guard to shield the introducer needle after use include Purdy, et al., U.S. Pat. Nos. 5,215,528; Rossetti, 5,201,713; Lemieux, 4,952,207; Dembrowski, 4,978,344; and Moorehead, 4,177,809. Each of these prior art patent discloses the use of a shield to cover the introducer needle after contact with potentially contaminated bodily fluids.

What these systems generally fail to address is the problem of blood flowback just after needle withdrawal. Once the needle is withdrawn, the catheter hub is open to low pressure venous blood flow until the infusion set is connected. A health risk is presented by this blood flowback. One prior device, the INTIMA IV CATHETER, manufactured by Becton Dickinson and Company has attempted to address this concern by placing a rubber seal at the proximal end of the catheter hub which reseals after needle withdrawal. However, this system does not address the problem of needle sticks. Further improvements are thus needed.

SUMMARY OF THE INVENTION

The present invention is embodied in a catheter introducing assembly which includes a self-shielding needle while providing captured visual blood flowback. The catheter introducing assembly embodying the present invention includes a clear Y-Connector which is used for contrast injection and has an additional port for medication. A V-Spring is placed unrestricted in a spring holder which is attached to the distal end of the Y-Connector. Once the needle is withdrawn, the spring acts as a guard, to prohibit forward movement of the needle.

An injection port is provided for high pressure introduction of medication or contrast media. A semi-spherical silicon ball is retained in the injection port which, when medication is required, will reseal after the needle is withdrawn.

A luer/filter assembly is provided in fluid communication with the introducer needle allowing air to escape through the filter for visualization of blood flowback upon needle insertion. The problem of blood flowback upon withdrawal of the needle is also addressed by providing a self sealing valve at the distal end of the tube.

The present invention is designed to protect the health care provider from inadvertent self-punctures and venous pressure blood flow contact. It is also designed to safely convey contrast media from the distal end of a catheter tube to the venous circulatory system of a patient utilizing a power injector, during a CT/MRI procedure, or any procedure requiring an IV Catheter.

BRIEF DESCRIPTION OF THE DRAWINGS

FIG. 1 is a plan view of the catheter needle assembly embodying the present invention illustrating the introducer in place within the catheter.

FIG. 2 is a plan view of the catheter needle assembly illustrated in FIG. 1 with the needle shown withdrawn from the catheter.

DESCRIPTION OF THE PREFERRED EMBODIMENT

A catheter introducer assembly 10 according to a preferred embodiment of the invention is shown in FIGS. 1, 2, 3, 4, 5, and 6.

Figure 3:
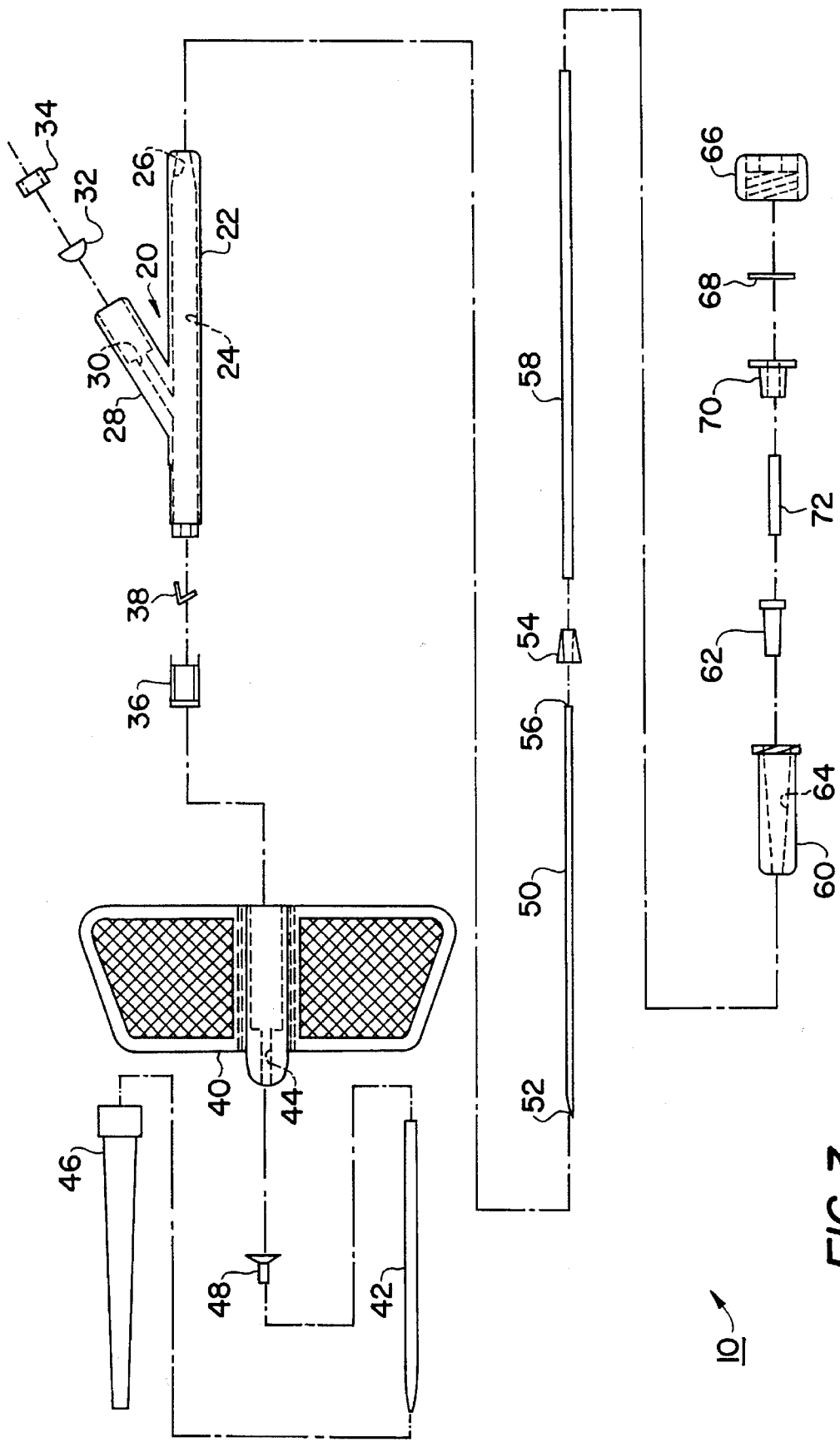
FIG. 3 is an exploded view of the components of the catheter needle assembly embodying the present invention.

The introducer assembly 10 employed in accordance with the preferred embodiment of the invention includes an integrally molded, transparent Y-connector body 20 which includes longitudinally disposed elongated body 22 in which is defined cylindrical passage 24 having proximal tapered seat 26. Referring more particularly to FIG. 3, access port arm 28 is formed integrally with body 22 and is obliquely oriented thereto. Access port arm 28 includes access channel 30 in fluid communication with passage 24. Semi-spherical silicon ball 32 is located within channel 30 and is held in place therein by retaining ring 34. The semi-spherical silicon ball is designed to plug fluid flow after needle withdrawal, by concentrating fluid forces inward to close the needle puncture site and be capable of withstanding fluid pressure of 350 psi with flow rates up to 10 ml/sec.

Spring holder collar 36 is fitted to the distal end of body 20 and is in fluid communication therewith to retain V-spring 38 in a position between body 20 and collar 36. The V-Spring 38 is compressed in its normal state proximate to needle 50. Upon withdrawal of needle 50, V-spring 38 opens and disables the needle from forward movement while allowing fluid flow. V-Spring 38 is designed to retain needle point 52 within body 20 after the needle has been withdrawn from catheter 42.

Wing member 40 is fitted to the distal end of body 24 to provide a handle for insertion of catheter 42. Wing member 40 also provides an anchor for the catheter upon insertion. Wing member 40 may be color coded to indicate catheter size or other information. Wing member 40 is flexible and designed for easy placement. The size of wing member 40 is large enough for additional taping which thereby secures positive placement of assembly 10.

Radiopaque catheter 42 is fitted to channel 44 defined in wing member 40 by catheter eyelet 48. The eyelet is placed into the catheter which is friction fit into wing member 40 to produce a non-leaking connection. Catheter protector cap 46 is provided to be fitted to wing member 40 to cover catheter 42 and needle 50 prior to use.

Hollow introducer needle 50 is slidably disposed within hollow catheter 42 with sharpened distal end 52 protruding from the distal end of catheter 42. The catheter tip is tapered both in both inner and out dimensions to produce a tight needle to catheter fit which will allow the catheter to follow the needle with relative ease into the vein.

Tapered needle connecting collar 54 is fitted to distal end 56 of needle 50, and also to blood collection tube 58 to maintain needle 50 and blood collection tube 58 in axial alignment and in fluid communication.

Collar 54, at its widest point, is substantially greater in diameter than tube 58 and, in use, is slidably disposed within passage 24 of body 20. Frustoconical collar 54 is mateable with seat 26 so that when the tube and needle assembly are withdrawn from the catheter, collar 50 will be restrained from further rearward movement by seat 26.

Female luer connector 60 is fitted to the distal end of collection tube 58. Duck bill valve 62 is disposed within passage 64 of female luer connector 60.

Filter cap 66 is adapted to be threaded to female luer connector 60 and is fitted with filter 68. Filter 68, in this embodiment, is a 2 micron filter, which is sized to permit the escape of air and to permit the flowback of blood through collection tube 58. Filter 68 is retained in filter cap 66 by tube holder 70. Valve tube 72 is fitted to tube holder 70.

The attachment of filter cap 66 to female luer connector 60 effects the insertion of tube 72 into duck bill valve 62, opening the valve so that needle 50, collection tube 58 and filter 68 are all in common fluid communication. When filter cap 66 is removed from luer connector 64, tube 72 is removed from valve 62, closing valve 62 to prevent the flow of blood out of the proximal end of tube 58.

The action of withdrawal of needle 50 into body 20 is illustrated between FIGS. 1 and 2. FIG. 1 illustrates the catheter introducer assembly 10 prior to use with protector cap 46 in place and needle 50 protruding through catheter 42. FIG. 2 illustrates catheter introducer assembly 10 with needle 50 withdrawn from catheter 42 into Y-connector body 20 until it is completely encased within passage 24 and collar 54 is stopped by seat 26. In this position the needle is completely shielded and the clinician is protected from the potentially contaminated needle.

Figure 4:
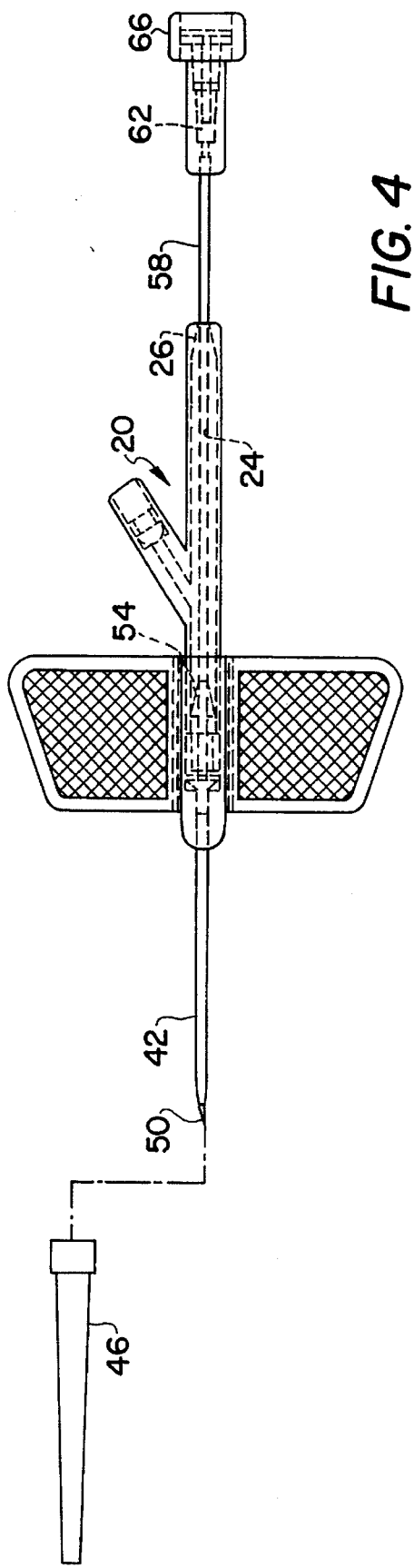
FIG. 4 is a plan view of the catheter needle assembly embodying the present invention illustrating blood flowback through the catheter assembly's introducer needle to indicate proper catheter placement.

FIG. 4 illustrates the introducer assembly 10 upon vascular introduction. In this view, appropriate catheter placement is indicated by blood flowback through needle 50 and tube 58. Normal vascular pressure is sufficient to urge blood through needle 50 and tube 58 since air relief is provided through filter 68. As previously described, filter 68 is a 2 micron filter which is sufficiently porous to allow the passage of air but not to allow the passage of bodily fluids. Also as previously described, fluid communication between tube 58 and filter 68 is maintained since duck bill valve 62 is held open by tube 72. Thus air escapes through filter 68 to allow blood flowback and indication of proper catheter placement.

Upon noting proper catheter placement in the vein, the clinician continues the procedure by pulling the needle and tube assembly out through the Y-connector. The needle and tube assembly is pulled until tapered connector 54 mates with tapered seat 26 in passage 24 in body 20.

Figure 5:
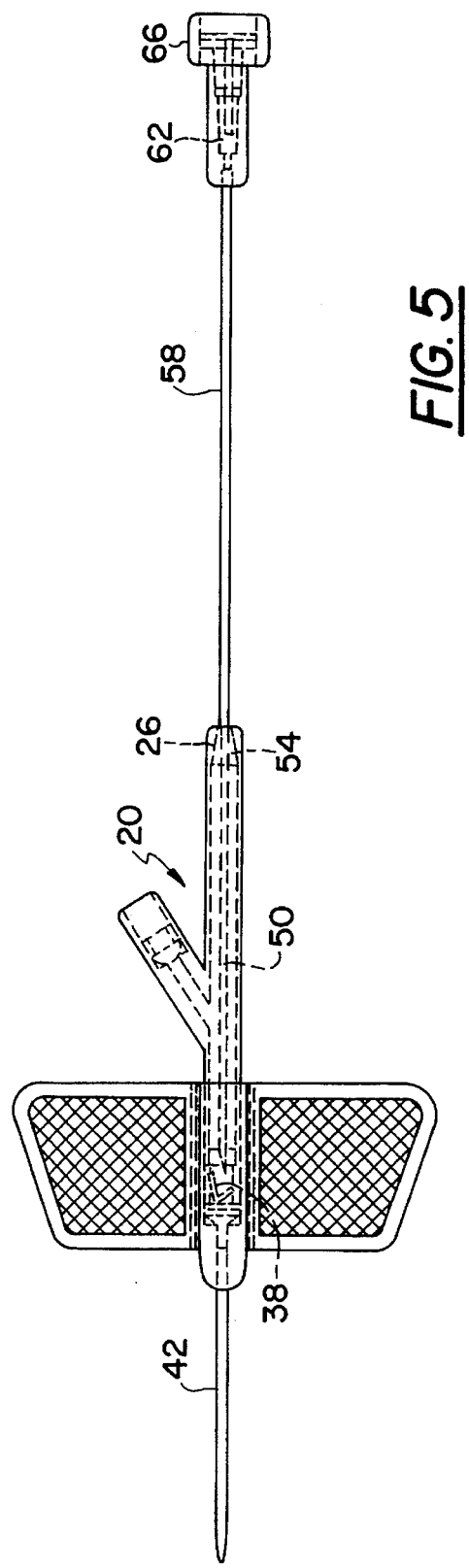
FIG. 5 is a plan view of the catheter needle assembly embodying the present invention illustrating the needle withdrawn into its self-storage housing.
Figure 6:
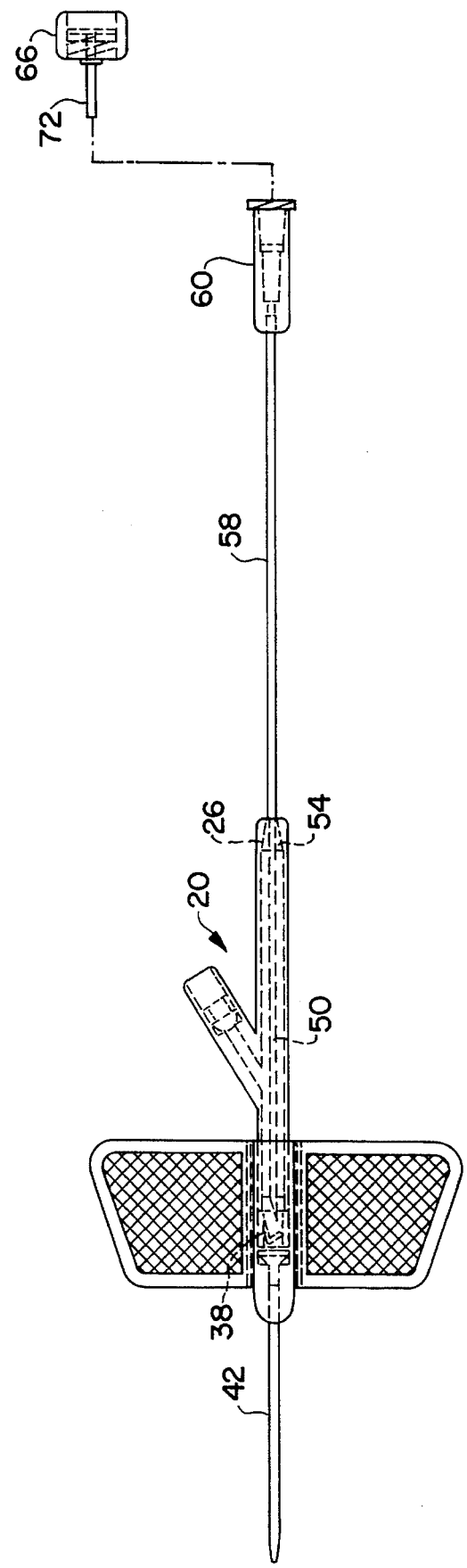
FIG. 6 is a plan view of the catheter needle assembly embodying the present invention illustrating the needle withdrawn into its self storage housing, with the unit's filter cap removed.

As shown in FIG. 5, V-spring 38 acts as a gate which is held open by the side of needle 50. When the needle and tube assembly are withdrawn, so that the point of needle 50 passes V-spring 38, the V-spring releases so that it is opened. Thus, V-spring 38 blocks passage 24 against any forward movement by needle 50 once it has been withdrawn past the V-spring. It is apparent, therefore, that needle 50 is then trapped within housing 20, restrained against forward movement by V-spring 38 and against rearward movement by seat 26.

In the next step of the procedure, the clinician removes filter cap 66 from luer connector 60, thus removing tube 72 from duck bill valve 62 and closing the valve. This closure acts to prevent blood from leaking out of the luer connector at the point of low pressure connection. The clinician may then connect an infusion set to female luer connector 60.

The intravenous catheter is now ready for injection of medication through access port 28. The relatively high injection pressure, in the area of 350 psi, will urge tapered connector 54 against tapered seat 26 to seal the proximal end of housing 20 against leakage. Medication may then be injected through access port 28 through a needle (not shown) piercing semi-spherical silicon ball 32. Upon removal of the medication needle from the access port, the silicon ball will reseal to prevent leakage through the access port.

What is claimed is:

1. A catheter introducer apparatus comprising:

a needle housing defining an elongated passage having a distal end in fluid communication with said catheter;

a needle slidably disposed within said catheter having a sharpened distal end adapted to protrude from said catheter;

filter means in fluid communication with said needle to allow air to escape therethrough while permitting blood flowback through said needle; and sealing means cooperating with said filter means to prohibit bloodflow through the catheter upon removal of the needle therefrom; wherein said filter means includes a filter valve associated with a proximal end of said needle, said filter valve having;

a valve housing in fluid communication with said needle;

a valve positioned within said housing; and a filter cap mateable with said valve housing and having valve opening means associated therewith mateable with said valve, so that attachment of said filter cap to said valve housing opens said valve, and removal of said cap closes said valve.

2. The catheter introducer apparatus as defined in claim 1 further including a luer connection mating said filter cap with said valve housing.

3. The catheter introducer apparatus as defined in claim 1 where said valve is a duck bill valve and said valve opening means is a valve tube adapted to open said duck bill valve and to maintain fluid communication between said needle and said filter 4. The catheter introducer apparatus as defined in claim 1 further including a filter associated with said filter cap and dimensioned to allow air flow but to impede the flow of bodily fluids under normal blood pressure.

5. The catheter introducer apparatus as defined in claim 1 wherein said filter valve further includes a 2 micron filter disposed within the filter cap.

6. The catheter introducer apparatus as defined in claim 1 further including an access port formed integrally with said needle housing defining an access passage in fluid communication with said needle housing passage; wherein said access port includes an elastomeric plug retained in said access passage adapted to be pierced by a fluid delivery needle to restrict fluid flow through said passage after withdrawal of said fluid delivery needle by concentrating fluid force inward to close a needle puncture in said elastomeric plug formed when said plug is pierced with said fluid delivery needle.

7. The catheter introducer apparatus as defined in claim 6 wherein said elastomeric plug is made of silicon.

8. The catheter introducer apparatus as defined in claim 6 wherein said elastomeric plug is semi-spherical in shape.

9. An intravenous catheter apparatus comprising:

a body housing defining an elongated body passage;

an intravenous catheter defining an elongated catheter passage, said catheter connected to said body such that the elongated body passage is in fluid communication with the elongated catheter passage;

a needle defining an elongated needle passage in fluid communication with said body passage and said catheter passage;

needle restriction means disposed between said needle and said body passage for allowing reward movement of said needle and prohibiting forward movement within said catheter;

needle retaining means contiguous with said body housing for retaining said needle within said body housing upon withdrawal from said catheter;

a valve connector axially engaged to a distal end of said body housing;

a valve cap engagable with said valve connector;

a blood filter disposed between said valve connector and said valve cap to allow the passage of air and retard the passage of blood; and a resilient, sealable robe disposed within said valve connector, said tube defining a resilient self sealing tubular passage.

10. The intravenous catheter apparatus according to claim 9, further comprising a high pressure fluid valve defining a high pressure fluid passage, said high pressure fluid valve connected to said body housing for introducing high pressure fluid therein and further comprising:

a sealable bead disposed within said high pressure fluid passage, wherein a high pressure fluid introduction needle may penetrate said sealable bead to introduce high pressure fluid therein.

11. A high pressure intravenous catheter for delivering high pressure fluid from a high pressure fluid source to a human being comprising:

a body housing defining a first elongated body passage and a second elongated body passage;

an intravenous catheter defining an elongated catheter passage, said catheter connected to said body such that the elongated body passage is in fluid communication with the first and second elongated catheter passages;

a needle defining an elongated needle passage, said needle slidably disposed within said catheter for retraction into the first elongated body passage, wherein said needle passage is in fluid communication with said first and second body passages and said catheter passage;

a high pressure connection valve disposed at a distal end of the second elongated body passage for providing high pressure fluid communication with said high pressure fluid source;

sealing means for halting intravenous blood flow through said body housing upon removal of said needle retraction means;

a valve connector axially engaged to a distal end of said body housing;

a valve cap engagable with said valve connector:

a blood filter disposed between said valve connector and said valve cap to allow the passage of air and retard the passage of blood; and a resilient, sealable tube disposed within said valve connector, said sealable tube defining a resilient self sealing tubular passage.

12. The high pressure catheter according to claim 11, further comprising a sealable bead disposed within said high pressure connection valve, wherein a high pressure fluid introduction needle may penetrate said sealable bead to introduce high pressure fluid therein.

13. The high pressure catheter according to claim 11, further comprising a spring disposed between said needle and said elongated body passage, whereby said spring extends to an unbiased position upon withdrawal of said needle.

* * * * *